(12) United States Patent
Hsu et al.

(10) Patent No.: US 9,370,613 B2
(45) Date of Patent: Jun. 21, 2016

(54) AXIAL-FLOW BLOOD PUMP

(71) Applicants: Po-Lin Hsu, Aachen (DE); Ulrich Steinseifer, Hauset (BE); Jack Parker, KN Vaals (NL); Ruediger Autschbach, Aachen (DE)

(72) Inventors: Po-Lin Hsu, Aachen (DE); Ulrich Steinseifer, Hauset (BE); Jack Parker, KN Vaals (NL); Ruediger Autschbach, Aachen (DE)

(73) Assignee: RHEINISCH-WESTFAELISCHE-TECHNISCHE HOCHSCHULE AACHEN, Aachen (DE)

( * ) Notice: Subject to any disclaimer, the term of this patent is extended or adjusted under 35 U.S.C. 154(b) by 0 days.

(21) Appl. No.: 14/395,337

(22) PCT Filed: Jul. 17, 2013

(86) PCT No.: PCT/EP2013/002120
§ 371 (c)(1),
(2) Date: Oct. 18, 2014

(87) PCT Pub. No.: WO2014/019646
PCT Pub. Date: Feb. 6, 2014

(65) Prior Publication Data
US 2015/0141739 A1 May 21, 2015

(30) Foreign Application Priority Data
Jul. 31, 2012 (EP) ..................................... 12005545

(51) Int. Cl.
*A61M 1/12* (2006.01)
*A61M 1/10* (2006.01)
*A61F 2/82* (2013.01)

(52) U.S. Cl.
CPC ............. *A61M 1/125* (2014.02); *A61M 1/1024* (2014.02); *A61M 1/1029* (2014.02); *A61M 1/1036* (2014.02); *A61F 2/82* (2013.01); *A61M 1/101* (2013.01); *A61M 1/122* (2014.02); *A61M 2205/04* (2013.01); *A61M 2205/103* (2013.01); *A61M 2210/12* (2013.01)

(58) Field of Classification Search
CPC ... A61M 1/125; A61M 1/1024; A61M 1/101; A61M 1/1029; A61M 1/1036; A61M 1/122; A61M 1/12
USPC .......................................................... 600/16
See application file for complete search history.

(56) References Cited

U.S. PATENT DOCUMENTS

| 2001/0031210 A1* | 10/2001 | Antaki | .................. | A61M 1/101 417/356 |
| 2006/0062672 A1* | 3/2006 | McBride | ............... | A61M 1/101 416/142 |

* cited by examiner

*Primary Examiner* — Paula J Stice
(74) *Attorney, Agent, or Firm* — Andrew Wilford

(57) ABSTRACT

An axial-flow blood pump has a rotatable impeller assembly rotatable about an axis and itself having a radially projecting blade and permanent magnets, A stationary stator assembly has stator windings interacting with the permanent magnets and a bearing system supporting the rotatable impeller assembly for rotation about the axis relative to the stator assembly. A stent implantable into a blood vessel is connected to ends of supports for coaxially mounting the stator assembly carrying the impeller assembly in the stent.

15 Claims, 4 Drawing Sheets

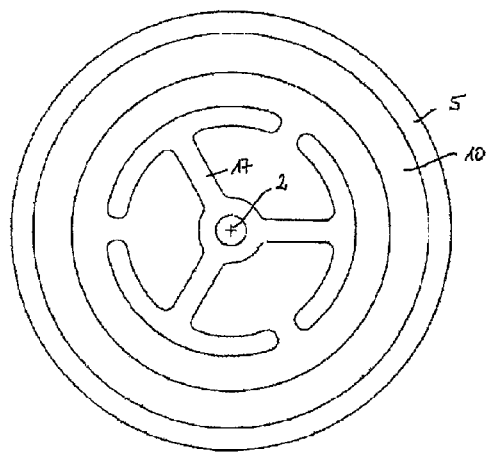
Fig. 6
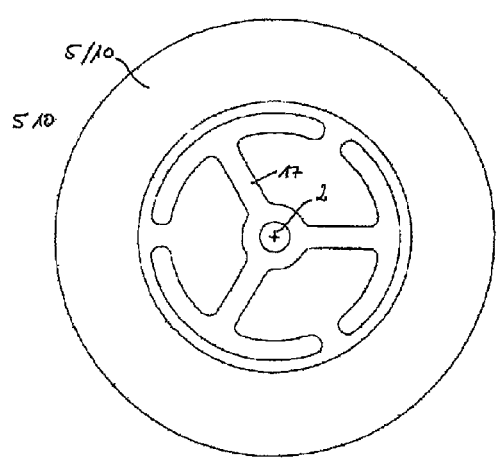
Fig. 7
Fig. 8
Fig. 9
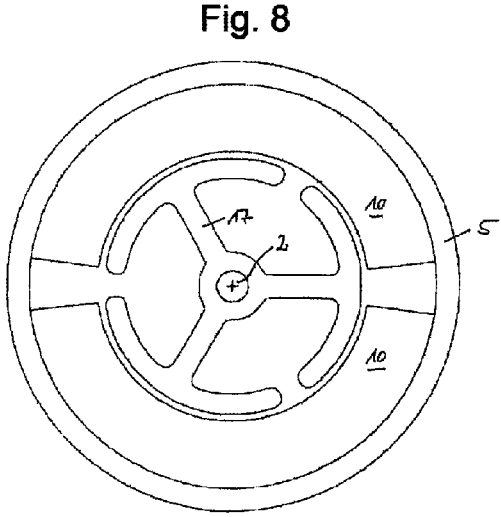
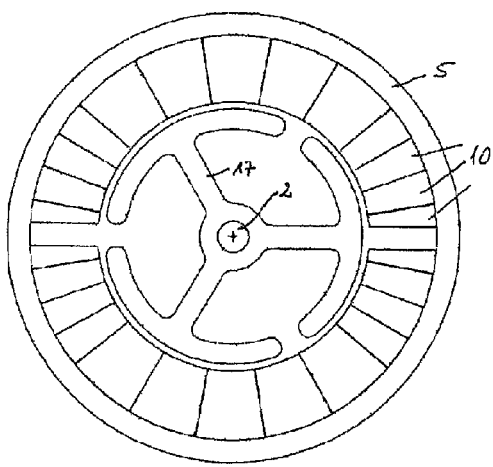

AXIAL-FLOW BLOOD PUMP

CROSS REFERENCE TO RELATED APPLICATIONS

This application is the US-national stage of PCT application PCT/EP2013/002120 filed 17 Jul. 2013 and claiming the priority of European patent application 12005545.4 itself filed 31 Jul. 2012.

FIELD OF THE INVENTION

The invention relates to an axial flow blood pump comprising an electromagnetic drive with a stationary stator assembly and a rotatable impeller assembly, wherein the stationary stator assembly at least comprises stator windings and a bearing system supporting the rotatable impeller assembly, the impeller assembly comprising at least one blade and permanent magnets interacting with the stator windings.

BACKGROUND OF THE INVENTION

Blood pumps of this kind are commonly known in the art and typically used to bridge a patient to recovery or heart transplantation in any kind of heart failure situations, particularly the end-stage patients who do not respond to medications.

Typically blood pumps of the common kind comprise a rigid housing and an inlet port and an outlet port, the housing furthermore comprising the aforementioned stator and impeller assemblies and the drive. As a consequence these blood pumps have a big volume requiring a placement in the thorax or abdomen and making it impossible to implant such a known blood pump in a minimally invasive implanting method. It is thus only beneficial to use these blood pumps for long-term application due to the invasiveness.

Due to this fact blood pumps, in particular for right ventricular assistance, are typically extracorporal and only available for short-term use. The duration of support and patient's quality of life is highly restricted by the extracorporal components, such as the drive and console. Implantable blood pumps exist; however, invasive surgeries, such as sternotomy or throracotomy, are required.

OBJECT OF THE INVENTION

Accordingly it is an object of the invention to provide a blood pump that may be implanted with minimally invasive techniques and allowing a long-term usage. It is furthermore an object of the invention to provide a blood pump that can also be applied as acute or short-term support due to the minimally invasiveness.

SUMMARY OF THE INVENTION

According to the invention this object is solved by a blood pump having a stationary stator assembly as mentioned before and furthermore comprising supporting elements for mounting, in particular coaxially mounting the device in the interior of an anchoring system that is implantable into a vessel.

It is an essential feature that a blood pump according to the invention does not have a typical rigid housing as known in the art for defining inlet and outlet port. A blood pump according to the invention is a conduit-free device for heart assistance, in particular right heart assistance. According to the invention the size of the device can be minimized to fit into an anchoring system by means of which it may be inserted into a vessel and fixed in it.

Preferably the anchoring system is used not to provide a conduit by the anchoring system itself but only to provide fixation in a vessel. Nevertheless, the anchoring system can be combined with some kind of conduit according to patient's condition, such as in patients with vessel disease. This anchoring system may be realized in one possible embodiment by a stent, which is implantable into a vessel, in particular by a stent that is customized for the purpose to function with the supporting elements.

Due to the attachment of the pump device to the anchoring system which is implantable/implanted into a vessel the vessel itself forms a conduit for the axial flow blood pump of the invention.

In a preferred embodiment the device is constructed as an embracing impeller system, meaning that the rotatable impeller assembly coaxially surrounds the stationary stator assembly, in particular coaxially surrounds a stationary shaft being a part of the stationary stator assembly. "Stationary" in this context means not moving in relation to the patient/the vessel of the patient.

According to this embodiment the stationary stator assembly may comprise a stationary shaft, stator windings surrounding the shaft, at least one winding holder for attaching the said windings to the shaft, a bearing system allowing the relative movement between the aforementioned components of the stationary stator assembly and the rotatable impeller assembly and the supporting elements for fixation. The bearing system rotatably connects the impeller assembly and the stator assembly.

The impeller assembly preferably comprises an impeller hub being coaxial with the shaft, permanent magnets being contained within the aforementioned impeller hub or making up the hub entirely and interacting with the stator windings, and at least one blade on the external surface of the hub.

The supporting elements are connected to the respective ends of the shaft, preferably to end parts covering the shaft ends. The supporting elements are used for mounting, in particular coaxially mounting the device in the interior of the implantable anchoring system.

According to the invention the blood pump may have a fixed attachment to an implantable anchoring system, like a stent, by means of the aforementioned supporting elements. In such an embodiment the anchoring system, in particular a stent is a part of the entire device.

In another embodiment the supporting elements may be detachable from the anchoring system and attachable to the said anchoring system. This allows detaching the pump device from the anchoring system at a certain time of usage in particular after full recovery of the heart or any emergency situations and removing the device from the patient and maintaining the anchoring system at its location where it is originally implanted.

In any way the supporting elements keep the axial and radial alignment of the pump device in the anchoring system. The profile of the supporting elements is preferably designed to overcome the load generated during the pump operation including the axial thrust force, fluid drag force, and radial twisting force. In a preferred embodiment, the supporting elements, in particular their cross section may have fluid dynamic shape to improve the pump efficiency.

To allow attachment and detachment each of the supporting elements may comprise a linking element at its distal area for linking to a corresponding element at or in the anchoring system. This linking element may be formed as a hook.

In a preferred embodiment each of the supporting elements may comprise a spring member or may totally consist of a spring member having an openable and closeable claw at the distal end for grabbing and releasing a mating part of an anchoring system. Generally a mating part of an anchoring system for connecting the supporting element may be the framework of the anchoring system itself or may be a connector part integrated into the framework of the anchoring system for this purpose.

A preferred embodiment of the said anchoring system may be a stent which is implantable into a vessel, in particular a stent that is customized for this purpose. The said stent may be used for anchoring the complete blood pump in the vessel. In particular the framework of a stent may be used for connecting the supporting elements. It is also possible to provide an additional connecting member in the sent.

According to the invention the anchoring system, in particular the stent may be collapsible/compressible/foldable as it is known in the art for common kinds of stents. In particular in combination with such a collapsible/compressible/foldable anchoring system/stent that may expand after implantation an improvement of the invention is given by the fact, that the at least one blade on the external surface of the hub is also collapsible/compressible/foldable thus reducing the cross section of the device in a collapsed/compressed/folded state.

Accordingly a system may be realized comprising such an inventive device and an anchoring system, in particular stent surrounding the device where the anchoring system and the device in particular the at least one blade and the supporting members of the device are in a collapsed/compressed state or some kind of folded state for implanting the whole system into a vessel where the system expands/unfolds after implantation, for example due to thermal or mechanical influence of the surrounding blood or by just releasing the system from an implantation tool, like a catheter. For this purpose the collapsed/compressed/folded and expandable parts of the system, in particular the stent and/or at least parts of the blade may be formed of shape memory alloys like nitinol.

A possible embodiment exists according to which the pump device may be inserted/implanted first into a peripheral vessel (like femoral or jugular vein) of a smaller diameter and then anchored in a main vessel (like pulmonary artery) of a larger diameter. This means the pump device has two distinct states, one has smaller size for implantation and explantation procedure and the other has a recovered size for operation. This reduceable size of the device allows for implanting the device with a minimally invasive method, for example by using a catheter.

The at least one blade of a device according to the invention may comprise at least one cantilever or a framework being hinged to the hub. This cantilever or framework may also form or define the geometry of the entire blade. The cantilever or framework may be movable between a first collapsed/compressed/folded position in which it is close to the hub or touching the hub and a second erected position when the device is implanted and in operation.

For example, the cantilever or framework may be rotatable in the hinge connection around at least one axis, preferably at least an axis parallel to the axis of rotation. A hinge connection with more than one axis of rotation may be for example a ball joint or hinge, in particular a spherical hinge. The cantilever or framework may have a distal side defining the blade tip and a proximal side where it is connected to the hub of the impeller assembly.

According to a preferred embodiment the proximal side of the cantilever or framework may be hinged to the hub in order to facilitate the folding process or providing the collapsed/compressed state.

The hinge may also comprise a stop member for stopping the movement of the cantilever/framework in the erected position thus preventing any movement and bending of the cantilever/framework or the entire blade beyond this erected position during operation.

Since the hydraulic loading may vary over the blade surface due to the nature of blade geometry and flow velocity, further reinforcement can be added within certain regions of the blade surface or the said framework in particular to avoid deformation during pump operation. This therefore avoids impaired pump efficiency resulting from deformation. Reinforcement may be realized by rods or plates of various dimensions interconnecting different areas/parts of the framework.

In a preferred embodiment the at least one cantilever or framework and the hub of the impeller may be covered with a biocompatible material, in particular with a flexible or elastic material. This material may also form a smooth surface for optimal flow path when the whole device is unfolded after implantation. Such a flexible or elastic material furthermore may sustain higher mechanical strain and stress without any plastic deformation thus allows for a better folding, when the device is collapsed/compressed/folded.

Preferably the elastic/flexible material also totally covers the joint/hinge at the proximal end of the cantilever or framework where it is connected to the hub and generates a smooth and streamline-optimized blood contacting surface. This prevents blood from clotting since it cannot get in contact with this hinge area.

In a preferred embodiment, at least part of the supporting elements may be collapsible/compressible/foldable as mentioned for the blade and/or anchoring system so the size of the entire pump system may be minimized for implanting and explanting procedure.

BRIEF DESCRIPTION OF THE DRAWING

Preferred embodiments of the invention are shown in the figures. Therein:

FIGS. 6, 7, 8, and 9 are end views of further embodiments of the invention.

SPECIFIC DESCRIPTION OF THE INVENTION

Figure 1:
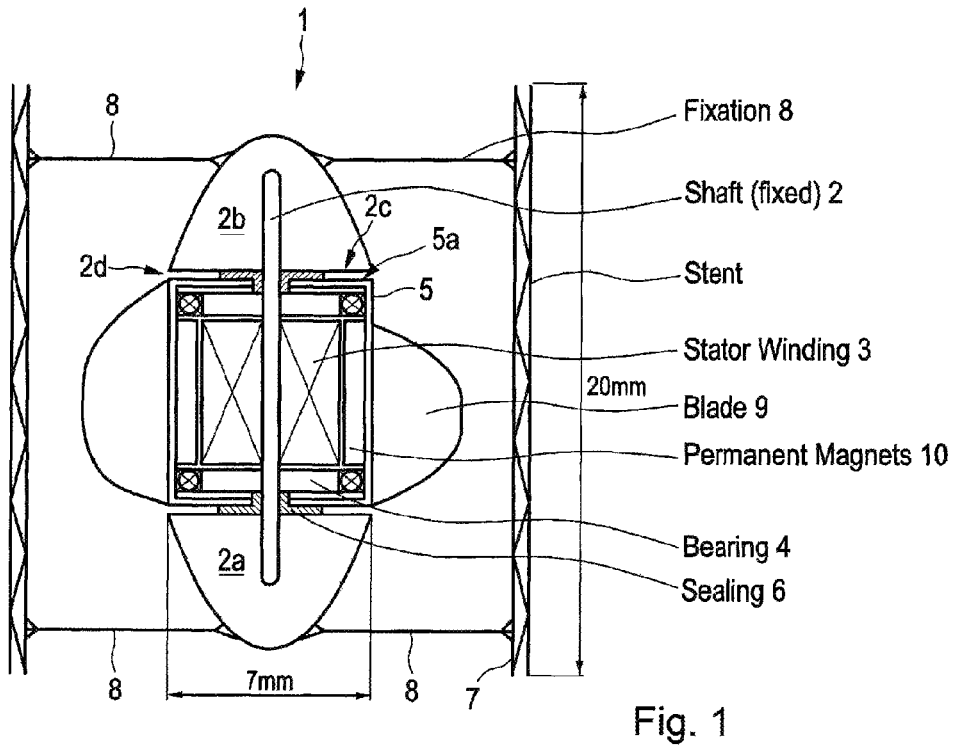
FIG. 1 is an axial section through a blood pump according to the invention.

FIG. 1 shows a cross-sectional view of one possible embodiment of the inventive blood pump 1 when it is coaxially located within the interior of an anchoring system 7 like a stent 7 implanted in a vessel (not shown).

The blood pump 1 comprises a fixed, stationary shaft 2 surrounded by stator windings 3 being held by at least one not shown winding holder and a bearing system comprising two bearings 4 near each axial end of the stator windings 3. Accordingly in operation of the device the shaft is not moving at all (with respect to the patient/vessel).

By means of these bearings 4 an impeller hub 5 is rotatable supported on this shaft 2. Any free spaces between the shaft 2 and the impeller hub 5 surrounding the shaft 2 may be closed by seals 6.

According to FIG. 1 respective end parts 2a and 2b cover the respective ends of the shaft 2 and are attached to the anchoring system 7 by means of supporting elements 8 which in this case extend essentially in radial direction between the respective end parts of the shaft 2 and the anchoring system 7 in order to position the device 1 in the anchoring system, preferably coaxially in the anchoring system 7 like a stent. The supporting element may also extend simultaneously in part radially and in part axially.

As shown in FIG. 1 the end parts 2a and 2b of the shaft 2 may be realized by fluid dynamically optimized caps which are attached to the shaft ends.

During operation of the blood pump 1, the anchoring system (stent) 7, the supporting elements 8, the shaft 2 and stator windings 3 are stationary and only the permanent magnets 10, the impeller hub 5 and the at least one blade 9 on the external surface of the hub 5 are rotating. The seals 6 in between the rotatable surface (of the impeller assembly) and the stationary surface (of the stator assembly) prevent the blood flowing into the internal space of the hub containing the windings and magnets.

The permanent magnets 10 which in this case are positioned on the internal surface of the hub are coaxially surrounding the stator windings and interacting with these windings in order to provide an electromagnetic rotational driving force for rotating the hub and the at least one blade.

According to the invention, the seal 6 may be made of magnetic fluid sealing or other known seals from common kinds of blood pumps.

In a possible embodiment that is applicable not only to the construction shown in the figure but generally to any possible embodiment, the sealing between the stationary stator assembly and the rotatable impeller assembly can be formed by the blood itself in a thin gap formed between a respective axial end part of the stator assembly and the rotatable axial abutting surface of the hub wherein a centrifugal repelling force can be generated from the rotation of the pump device.

Such a gap may be realized by a distance between two facing surfaces perpendicular to the axis of rotation, preferably by a distance between the inner axial abutting surface of the cap/end part of the shaft and the axial abutting face of the hub. In FIG. 1 these facing surfaces are given by 2c and 5a and the gap by 2d.

A centrifugal repelling force during operation may generate a fluid film preventing the blood to flow into the unwanted area. Such a sealing may also be used in addition to a mechanical or the aforementioned magnetic fluid sealing that prevents blood from flowing in unwanted areas during standstill of the device, in particular during implantation.

Figures 2A, 2B:
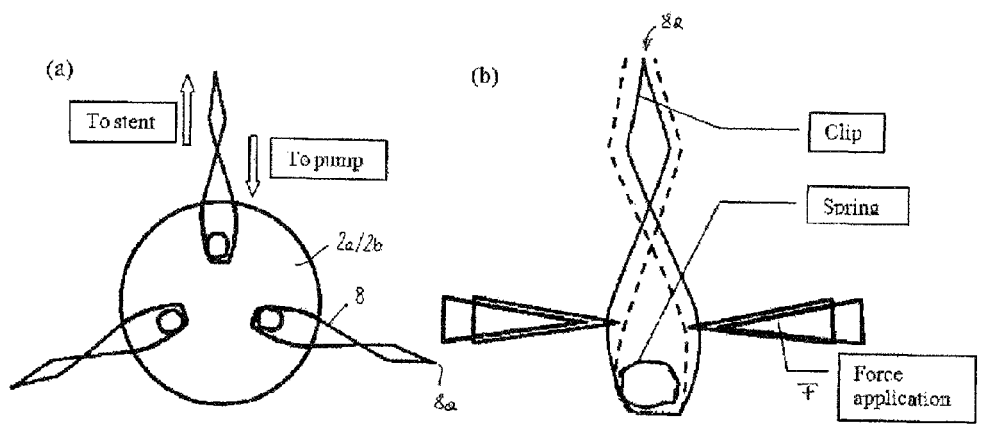
FIGS. 2a and 2b are small-scale end and top views of the inventive blood pump.
Figure 3A:
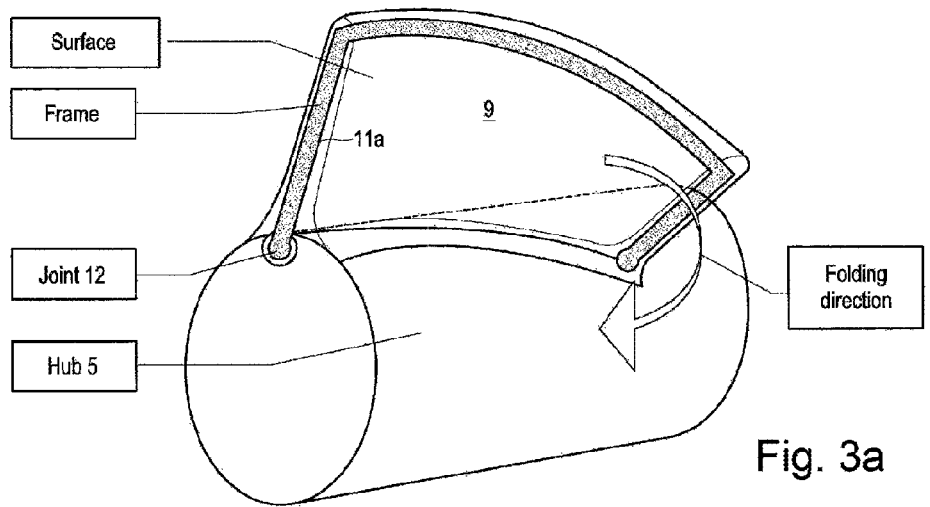
FIGS. 3a, 3b, 3c, 3d, and 3e are views of different blades on a hub according to the invention.
Figure 3B:
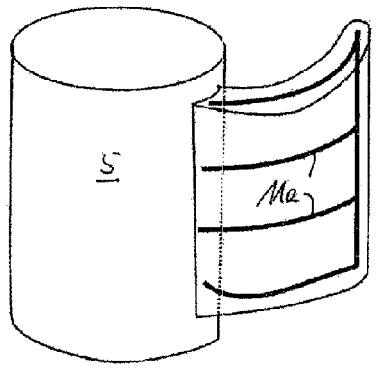
Figure 3C:
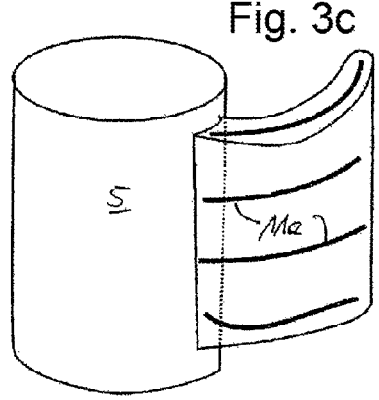
Figure 3D:
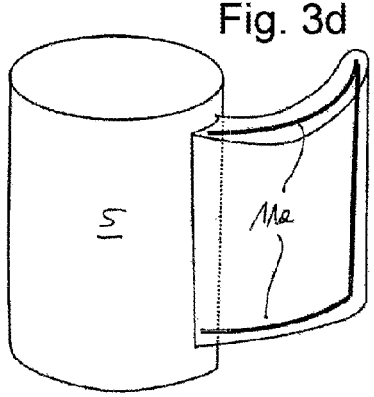
Figure 3E:
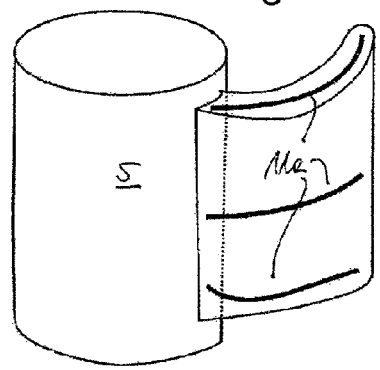

FIGS. 2a and 2b show a possible embodiment according to which the support elements 8 comprise or totally consist of spring element forming a claw 8a at its distal end in order to grab or release a mating part of the stent 7. According to FIGS. 2a and 2b the spring element may be formed as a crossed wire for example of metal or any other kind of material opening and closing the distal end when a force F is applied or released in a direction perpendicular to the radial extension of the support element.

According to FIGS. 2a and 2b, the supporting elements 8 of any kind of construction and in particular the construction shown in FIGS. 2a and 2b may be hinged to the respective end part 2a/2b of the shaft 2 thus allowing for folding or collapsing or compressing also these supporting elements 8 in order to allow the reduction of the cross section of the inventive device for implantation with a minimally invasive method.

Also in another possible embodiment the spring element and claws 8a of the supporting elements 8 may be made of flexible or elastic material to enable folding or collapsing or compressing process with the pump system.

The supporting elements 8 of any kind of construction and in particular the construction shown in FIGS. 2a and 2b are designed to withstand the loads induced from the pump operation, such as the axial thrust force, twisting toque, and fluid drag forces.

Also, the aforementioned hinges of any kind of construction and the mating parts on the anchoring system connected to the supporting elements preferably have a profile that can withstand the aforementioned loads during pump operation.

As already mentioned in the general part of the description in a preferred embodiment also the at least one blade on the external surface of the hub is collapsible or compressible or at least foldable in order to reduce the cross section of the impeller and the total device.

Accordingly the blood pump can be inserted into peripheral vessels like the femoral or jugular veins in collapsed/folded state and may expand to its original form for operation at a target vessel like the pulmonary artery. Once the pump is successfully implanted, anchored in the said target vessel by means of a stent or another anchoring system and fixed to it by means of the support elements at the respective shaft ends, the impeller driven by the electric motor may start to rotate.

Foldable components of the invention preferably include the at least one impeller blade, the anchoring system like a stent and the support elements which extend between the shaft ends or the end parts and the anchoring system. Preferably the blade is foldable but still robust enough to prevent bending or twisting due to hydraulic loading acting on the surface during operation.

For this purpose the blade may comprise at least one cantilever or a framework 11 that may define the geometry of the blade as shown in FIGS. 3a-3e. In addition to forming the geometry of at least the blade edges the cantilevers of framework 1 are also capable of reinforcing the blade during pump operation. In addition the framework or cantilever may have additional structural features that can optimize the loading distribution of the cantilever or framework for example by varying the thickness of the framework or providing holes in framework or interconnecting rods. The framework 11 may comprises several rods 11a extending away from the hub. These rods may be interconnected. For providing foldability the framework/cantilever 11 is hinged to the hub in hinges/joints 2.

FIGS. 4 and 5 show the possible embodiments of a hinge 12 which may be used to connect the cantilever or framework 11 to the hub 5. This may relieve the stress induced from folding the connecting area between cantilever/framework 11 and hub 5.

Figure 4A:
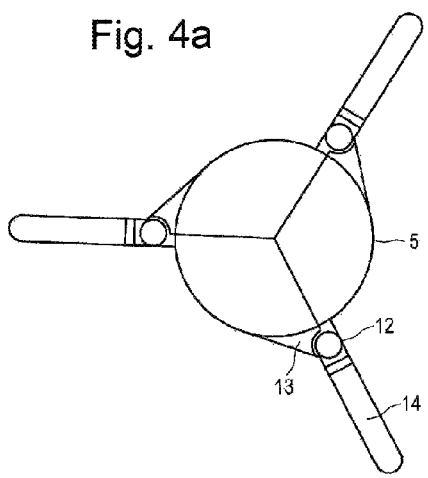
FIGS. 4a and 4b are end views showing the cantilever or framework in the extended/erect position and folded position.
Figure 4B:
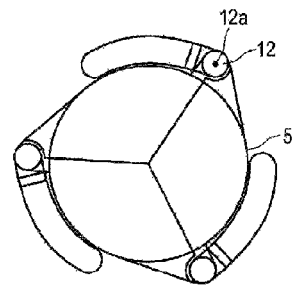

As can be seen in FIGS. 4a and 4b a hinge 12 may have an axis of rotation 12a being positioned outside the maximum radius of the hub 5. The hinge 12 may provide a stop element 13 for stopping the movement of the cantilever or framework 14 when reaching the erected position as shown in the upper part of FIGS. 4a and 4b. As shown in lower part of FIGS. 4a and 4b the cantilever or framework may be flexible and may be formed or bended in accordance with the surface of the hub in the collapsed state.

Figure 5A:
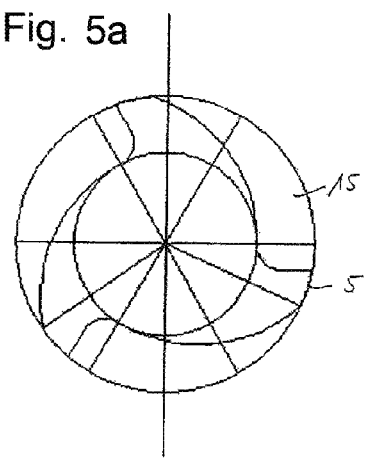
FIGS. 5a and 5b are also end views of another variant on the invention in various positions.
Figure 5B:
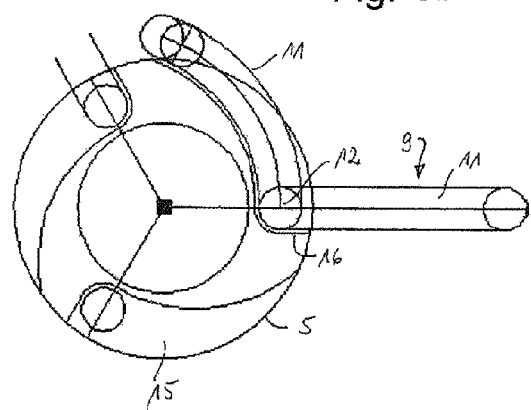

Also, as shown in FIGS. 5a and 5b the hub 5 of the impeller may have recesses 5 extending in a circumferential direction and accommodating the cantilever or framework 11 or the blade 9 at least partially when the blade 9 is in a compressed/ collapsed or folded position. The recesses may have a radial depth decreasing with increasing circumferential extension. In FIGS. 5a and 5b the axis of the hinge 12 is positioned underneath the circumferential surface of the hub 5 or inside the maximum radius of the hub 5. Accordingly a wall part of the recess 15 may also form a stopping element 16 for stopping the movement of cantilever or framework 11 when reaching the erected position as shown in the lower part of FIGS. 5a and 5b.

It is obvious from the figures that a blood pump according to the invention provides a small cross section when it is in a collapsed/compressed or folded state thus may be implanted together with a compressed/collapsed anchoring system like a stent using a minimally invasive method. For example a system of a blood pump according to the invention and a stent may be implanted using a catheter.

In all the embodiments discussed in the general part and the embodiments of the figures the electrical motor is totally beatable/located in the interior of the anchoring system/stent preferably between the stationary shaft and the hub of the impeller.

An electrical power supply may be connected to the stator windings by cables. The power supply may be also implanted or may be extracorporal. It is also possible to provide power to the device according to the invention by means of induction. In such a case there is no need to implant a power source. A receiver for receiving electro-magnetic power waves may be integrated into the device or coupled to it via cables and implanted in the thorax. A sender may be placed in surface contact with the skin.

The integrated motor may be a brushless permanent magnet motor having a high power density. The motor is composed of the stator assembly containing a set of excitation coils to drive the impeller which contains the permanent magnets in the interior of the hub.

The motor can be an external rotor motor where the impeller assembly locates outside the stator assembly or an internal rotor motor where the impeller assembly locates inside the stator assembly but is preferably according to the invention and in accordance with FIG. 1 of the external type. In the external-rotor embodiment the entire motor is implemented into the impeller assembly or its hub without efficiency reduction resulting from an air gap between the magnets and the winding as usually be known from common kinds of blood pumps.

In contrast to other blood pumps having a prolonged rotated shaft extending outside the body, the device according to the invention comprises an electromagnetically drive which is fully integrated into the device without having any extracorporal motor components and the mechanical wear of the prolonged rotated shaft. This allows for better patient's quality of life and a longer support duration in comparison to other known pumps.

In addition the motor, preferably an external rotor motor, in the invention is minimized and optimized to a volume that is unique to unusually known kinds of motors, especially existing external rotor motors.

The design shown in FIG. 1 and in general the external rotor design significantly reduces the volume of the stator and the available winding area. To accommodate sufficient coils in a limited space while avoiding high magnetic saturation in the back iron of the stator geometry and ratio between permanent magnet thickness and stator diameter need to be carefully designed and optimized.

In accordance to the invention in all of the possible embodiments the stator may have a back iron as it is conventionally known or may be totally ironless. A conventional stator can conduct magnetic field path better due to the high permeability and provide a solid frame to hold the windings. On the other hand an ironless stator which has only coils making up the stator has the advantage of zero iron loss and minimal heat generation in the stator. For reducing iron loss in the conventional design a laminated stator may be used.

Another advantage of an ironless motor is that such motors may be started without the need to overcome static attraction force. Accordingly it is easy to start an ironless motor and generate smoother motor operation.

The FIGS. 6 to 9 show cross-sectional views of possible designs of the drive of the device according to the invention i.e. of the stator windings and the permanent magnets.

In any external-rotor embodiment of the rotatable impeller assembly design the permanent magnets 10 are surrounding the winding holder 17 and the windings (not shown) and have a pole number in correspondence with the stator winding. In a preferred embodiment, the pole number is two for the output demand of this pump application. The poles made of permanent magnets 10 of the impeller assembly are radially aligned along the inner circumference of the hub 5 in accordance with FIG. 8. The magnet pole may comprise segmented strips or bars as shown in FIG. 9.

In another embodiment the permanent magnets 10 may form a hollow cylinder 10 underneath the hub 5 according to FIG. 6 or a hollow magnetical cylinder may form the hub itself, as shown in FIG. 7. The magnet span angle or the span angle of magnetization may be modified for optimal motor efficiency. FIG. 10 shows another embodiment according to which each pole consists of several permanent magnet pieces 10 having different circumferential length. Furthermore, in FIG. 9 the permanent magnet pieces 10 may have different magnetization strength.

In the preferred embodiment the direction of magnetization of the said permanent magnet/s point radially inwards or outwards. In another embodiment, parallel magnetization may be used. The magnetic field may be further optimized. This may be done by altering direction and/or strength of magnetization in each permanent magnet pieces 10. This flexible combination may be realized by the segmented magnet pole.

Also the material of the hub may be magnetic-conducting materials or nonmagnetic-conducting materials, resulting in different magnetic field distribution in the motor. Radial span and magnetization direction/strength of the permanent magnets have to be altered for different configurations to generate optimal motor efficiency. In one possible embodiment, the permanent magnet may make up the hub as mentioned and shown in FIG. 7.

In any embodiment, the rotatable impeller assembly may be radially centered to the stator shaft 2 by the said bearing system. The bearing system allows the relative rotation between the said stationary stator assembly and the said rotatable impeller assembly. In one possible embodiment, the bearing system may be mechanical ceramic ball bearings or pivot bearings.

According to the innovations above, this invented device has the advantages as described below:

1. Long-term right heart support that can be implanted/inserted minimally invasively.

2. The device proposed can offer flexible type of support, ranging from short to long term bridge therapies, which benefits wider range of patients 3. The in-series operation without bypassing the ventricle reduces the complications associated with invasive cannulation. In addition, the device poses minimal effects to the native heart valve.

4. The fixation mechanism allows easy removal of the device when the patient is weaned or in case of device failure.

The bio-compatible anchoring system/stent stays in the vessel to avoid the harmful rupture to the blood vessel lumen.

5. The integrated drive motor allows possible reduction in system length to ease the insertion during guidance through the intra-vascular or intracardiac curvatures.

6. Combination of integrated motor and foldable impeller enables the blood pump generating the same output at a lower speed compared to those miniature impeller pumps. Therefore, the risk or hemodynamic complication can be minimized and the device life span as well as the support duration can be significantly elevated.

The invention claimed is:

1. An axial-flow blood pump comprising:
   a rotatable impeller assembly rotatable about an axis and having
      a radially projecting blade, and
      permanent magnets;
   a conduit-free stationary stator assembly having
      stator windings interacting with the permanent magnets, and
      a bearing system supporting the rotatable impeller assembly for rotation about the axis relative to the stator assembly;
   an anchoring system implantable into a blood vessel; and
   supports for coaxially mounting the stator assembly spaced radially inward from the anchoring system while permitting axial blood flow in the vessel between the assemblies and the anchoring system.

2. The blood pump according to claim 1, wherein the supports have hydrodynamically optimized shape.

3. An axial-flow blood pump comprising:
   a rotatable impeller assembly rotatable about an axis and having
      a hub centered in the axis,
         a blade fixed on and projecting radially from the hub, and
      permanent magnets fixed in the hub; and
   a stationary stator assembly having
      a stationary shaft extending along the axis through the hub, and
         stator windings surrounding the shaft surrounded by the hub, and interacting with the permanent magnets of the impeller assembly;
   a bearing system supporting the shaft and windings of the rotatable impeller assembly for the rotation about the axis relative to the stator assembly;
   an anchoring system implantable into a blood vessel; and
   supports fixed at ends of the shaft for coaxially mounting the states assembly carrying the impeller assembly in the anchoring system.

4. The blood pump according to claim 3, wherein the permanent magnets align radially in the hub or make up the hub.

5. The blood pump according to claim 4, wherein the permanent magnets are formed by segmented magnet stripes or bars having different radial span and/or different magnetization strength or are formed by a complete hollow cylinder coaxially with the shaft.

6. An axial-flow blood pump comprising:
   a rotatable impeller assembly rotatable about an axis and having
      a radially projecting blade, and
      permanent magnets; and
   a stationary stator assembly having
      stator windings interacting with the permanent magnets, and
      a bearing system supporting the rotatable impeller assembly for rotation about the axis relative to the stator assembly;
   a stent implantable into a blood vessel; and
   supports having ends detachably fixed in the stent for coaxially mounting the stator assembly carrying the impeller assembly in the stent.

7. The blood pump according to claim 6, wherein each of the supports comprises or consists of a spring member having an openable and closable claw for grabbing and releasing a mating part of the stent.

8. An axial-flow blood pump comprising:
   a rotatable impeller assembly rotatable about an axis and having
      a hinge,
      a radially projecting blade having a framework carried on the hinge and pivotal between an outer erected position and an inner collapsed, compressed, or folded position, whereby when in the inner position the blade is of reduced axial cross section, and
      permanent magnets; and
   a stationary stator assembly having
      stator windings interacting with the permanent magnets, and
      a bearing system supporting the rotatable impeller assembly for rotation about the axis relative to the stator assembly;
   an anchoring system implantable into a blood vessel; and
   supports for coaxially mounting the stator assembly carrying the impeller assembly in the anchoring system.

9. The blood pump according to claim 8, wherein the hinge has a stop member stopping the movement of the framework in the erected position.

10. The blood pump according to claim 8, wherein an outer surface of the hub is formed with recesses at least partially accommodating the collapsed/compressed/folded framework or the entire blade in the inner position of the blade.

11. The blood pump according to claim 8, wherein the at least one framework and the hub are covered with a biocompatible flexible material.

12. An axial-flow blood pump comprising:
   a rotatable impeller assembly rotatable about an axis and having
      a radially projecting blade, and
      permanent magnets;
   a stent implantable in a blood vessel; and
   a stator assembly spaced radially inward from the stent and having
      stator windings interacting with the permanent magnets, and
      a bearing system supporting the rotatable impeller assembly for rotation about the axis relative to the stator assembly; and
   supports for coaxially mounting the stator assembly carrying the impeller assembly in the stent.

13. The axial-flow blood pump defined in claim 12, wherein the supports extend radially between the stent and the stator assembly.

14. The axial-flow blood pump defined in claim 12, wherein the supports are foldable or collapsible so that the stent and supports can be pressed against an outer surface of the assemblies for insertion of the pump into the blood vessel.

15. The axial-flow blood pump defined in claim 14, wherein the blade is also radially foldable or collapsible.

* * * * *